United States Patent [19]
Baszczynski et al.

[11] Patent Number: 5,824,870
[45] Date of Patent: Oct. 20, 1998

[54] COMMERCIAL PRODUCTION OF APROTININ IN PLANTS

[76] Inventors: Chris Baszczynski, 7305 Benton Dr., Urbandale, Iowa; Thomas Czapla, 4624 70th Pl., Urbandale, Iowa 50322; Elizabeth Hood, 9265 Lincoln Ave., Clive, Iowa 50325; Terry EuClaire Meyer, 4338 101st St., Urbandale, Iowa 50322; David Peterson, 6219 Willow Crest Dr., Apart. 202, Johnston, Iowa; A. Gururaj Rao, 4734 74st St., Urbandale, Iowa 50322; James C. Register, III, 1710 Maxwell Ave., Ames, Iowa; Derrick Witcher, 4726 93rd St., Urbandale, Iowa 50322; John A. Howard, 2976 NW. 132nd Ct., West Des Moines, Iowa

[21] Appl. No.: 554,161

[22] Filed: Nov. 6, 1995

[51] Int. Cl.$^6$ .......................... C12N 15/29; C12N 15/82; C12N 15/12; A01H 5/00
[52] U.S. Cl. ................................. 800/205; 800/DIG. 56; 800/250; 435/172.3; 435/240.4; 435/320.1; 435/69.1; 435/69.2; 435/69.8; 536/23.5; 536/24.1
[58] Field of Search .................... 435/69.1, 69.2, 435/69.8, 172.3, 240.4, 320.1; 536/23.5, 24.1; 800/205, 250, DIG. 56

[56] References Cited

U.S. PATENT DOCUMENTS

| | | | |
|---|---|---|---|
| 4,894,436 | 1/1990 | Auerswald et al. | 530/324 |
| 4,914,025 | 4/1990 | Manoil et al. | 435/69.8 |
| 4,956,282 | 9/1990 | Goodman et al. | 435/69.51 |
| 5,460,952 | 10/1995 | Yu et al. | 435/69.1 |

FOREIGN PATENT DOCUMENTS

| | | | |
|---|---|---|---|
| 0 348 348 | 12/1989 | European Pat. Off. | A01N 65/00 |
| 0 672 754 | 9/1995 | European Pat. Off. | C12N 15/83 |
| WO 90 01551 | 2/1990 | WIPO | C12N 15/82 |
| WO 91 02066 | 2/1991 | WIPO | C12N 15/62 |
| WO 92 01048 | 1/1992 | WIPO | C12N 15/00 |
| WO 93 21320 | 10/1993 | WIPO | C12N 15/29 |
| WO 94 16565 | 8/1994 | WIPO | A01N 63/00 |
| WO 95 14099 | 5/1995 | WIPO | C12N 15/82 |

OTHER PUBLICATIONS

Goddign, et al "Plants as Bioreactors", Trends in Biotechnology 13: No. 9(Sep. 1995).

During et al Synthesis and self-assembly of functional monoclonal antibody in transgenic *Nicotiana tabacum*:, Plant Molecular Biology 15:281–293 (1990).

Cornejo et al. Activity of a maize ubiquitin promoter in transgenic rice. Plant Molecular Biology 23: 567–581, 1993.

Gordon–Kamm et al. Transformation of maize cells and regeneration of fertile transgenic plants. The Plant Cell, vol. 2, 603–618, Jul. 1990.

Murray et al. Codon usage in plant genes. Nucleic Acids Research, vol. 17, No. 2, 1989.

Laskowski, Jr. et al., "Protein Inhibitors of Proteinases", Ann. Rev. Biochem., vol. 49, pp. 593–626, (1980).

Creighton et al., "Sequences of the Genes and Polypeptide Precursors for Two Bovine Protease Inhibitors", J. Mol. Biol., vol. 194, pp. 11–22, (1987).

Jeffrey et al., "Pathology of the Transmissible Spongiform Encephalopathies with Special Emphasis on Ultrastructure", Micron., vol. 26, No. 3, pp. 277–298, (1995).

Smith et al, "Molecular Pathology of Prion Diseases", Essays in Biochemistry, vol. 29, pp. 157–175, (1995).

Berman Marks et al., "Mutants of Bovine Pancreatic Trypsin Inhibitor Lacking Cysteines 14 and 38 Can Fold Properly", Science, vol. 235, pp. 1370–1373, (1987).

Auserwald et al., "Expression, Isolation and Characterization of Recombinant [Arg$^{15}$, Glu$^{52}$] Aprotinin" Biol. Chem. Holppe–Seyler, vol. 369, Suppl., pp. 27–35, (1988).

Kassell, "Bovine Trypsin–Kallikrein Inhibitor (Kunitz Inhibitor, Basic Pancreatic Trypsin Inhibitor, Polyvalent Inhibitor from Bovine Organs)", Naturally Occurring Activators & Inhibit., pp. 844–853.

*Primary Examiner*—Douglas W. Robinson
*Assistant Examiner*—Thomas Haas
*Attorney, Agent, or Firm*—Patricia A. Sweeney

[57] ABSTRACT

A method for commercial production of aprotinin entails heterologous expression of the protein in plants, preferably at a level such that aprotinin accounts for at least 0.1% of the total extracted protein. An aprotinin-expressing plant also has potential of increased insecticidal resistance by virtue of producing the protein. A genetic map of the integration locus allows identification of plants derived from the transgenic plant. This approach also reveals genetic loci on a plant chromosome that support high levels of gene expression and can be used as site of integration for expression of other genes of interest.

13 Claims, 2 Drawing Sheets

```
  1 GGATCCCAAC AATGGCCAAC AAGCACCTGA GCCTCTCCCT CTTCCTCGTG
 51 CTCCTCGGCC TCTCCGCCTC CCTCGCCAGC GGCCGCCCGG ACTTCTGCCT
101 CGAGCCGCCA TACACCGGAC CCTGCAGGGC CAGGATCATC CGCTACTTCT
151 ACAACGCCAA GGCCGGCCTC TGCCAGACCT TCGTGTACGG AGGCTGCCGC
201 GCCAAGCGCA ACAACTTCAA GAGCGCTGAG GACTGCGAGC GCACCTGCGG
251 AGGCGCCTGA TATCGTCGAC GAATTC
```

COMMERCIAL PRODUCTION OF APROTININ IN PLANTS

BACKGROUND OF THE INVENTION

Aprotinin is a protease inhibitor, also referred to as "bovine pancreatic trypsin inhibitor," which affects known serine proteases such as trypsin, chymotrypsin, plasmin and kallikrein. Aprotinin is a single, 58 amino-acid polypeptide which has a molecular weight of 6511 daltons; its structure, folding, and activity have been amply documented. See, for example, Fritz et al., *Arzneimittelforsch,* 33: 479–94 (1983); Deisenhofer et al., *Acta Crystallogr., Sect. B,* 31: 238–50 (1975); Laskowski et al., *Ann. Rev. Biochem.* 49: 593–626 (1980); Creighton, *Ann. Biophys. Mol. Biol.* 33: 231–97 (1978). The bovine aprotinin gene has been identified. Anderson et al., *Proc. Nat'l Acad. Sci. U.S.A.* 80: 6838–42 (1983); Kingston et al., *Biochem. J.* 233: 443–50 (1986); Creighton et al., *J. Mol. Biol.,* 194: 11–22 (1987).

Purified aprotinin is used as a research tool in molecular biology and as a therapeutic agent. For commercial exploitation, aprotinin is currently purified from bovine pancreas and lung. There are two problems associated with aprotinin derived from bovine organs. Cost of storing the raw material is high. More important for aprotinin as a therapeutic agent, there are concerns about it being contaminated with prions. Goodbrand et al., *Micron,* 26:(3) 277–298 (1995) and Smith, C. and Collinge, Jr. *Essays in Biochemistry,* 29: 157–174 (1995).

For commercial development it might be desirable to express the aprotinin gene in systems other than mammalian cells. In order to test folding and expression in systems other than mammalian cells, synthetic aprotinin or genes which encode aprotinin with a modified primary amino acid (aa) sequence were constructed. Generally, aprotinin with a modified aa sequence had lower activity. See Schnabel et al., *Biol. Chem. Hoppe-Seyler* 367: 1167–76 (1986); Marks et al., *Science,* 235: 1370–3 (1987); v. Wilken-Bergman et al., *EMBO J.,* 5: 3219–25 (1986); Auerswald et al., *Biol. Chem. Hoppe-Seyler* 368: 1413–25 (1987); Tschesche et al., *Methods Enzymol.* 45: 772–85 (1976); and Auerswald et al., *Biol. Chem. Hoppe-Seyler* 369: 27–35 (1988).

Expression of foreign genes in plants is amply documented. In general, the expression of the foreign gene has been desired for the benefit of the plant, for example, by the action of expressed antifungals or growth factors; to improve an agronomic trait, such as fruit ripening or nutritional content; or to induce sterility in the context of creating hybrid plants. It also is feasible to express in plants heterologous genes, expressing high value products. In many cases, expression in plants could be the system of choice, because of such inherent advantages such as cost relative to that of tissue culture, and the concern about correct glycosylation and other post-translational processing of the expression product from other expression systems.

The level of protein expression in plants can be influenced by many factors. One factor is the choice of transcriptional promoters used. Recently, the range of available plant compatible promoters has increased to include tissue specific and inducible promoters. Some of the better documented constitutive promoters include the CaMV 35S promoter and the ubiquitin promoter. See Kay et al., *Science* 236: 1299 (1987), and European patent application No. 0 342 926. Yet other factors that can be manipulated to control levels of expression are the presence of transcriptional modification factors such as introns, polyadenylation and transcription termination sites. At the translational level, other factors to consider are the ribosomal binding site and the codon bias of the gene. High level expression of a gene product which then accumulates in the cytoplasm may result in toxicity to the plant cell; removal of the gene product from the cytoplasm thus may result in overall higher expression levels. Furthermore, intron sequences within the aprotinin gene may also increase its expression level by stabilizing the transcript and allowing its effective translocation out of the nucleus. Most plant genes contain intron sequences. Among the known such intron sequences are the introns of the plant ubiquitin gene. Cornejo et al., *Plant Molec. Biol.* 23: 567–581 (1993). Furthermore, it has been observed that the same construct inserted at different loci on the genome can vary in the level of expression in plants. The effect is believed to be due at least in part to the position of the gene on the chromosome, i.e., individual isolates will have different expression levels. See, for example, Hoever et al., *Transgenic Res.* 3: 159–66 (1994) (report regarding constructs containing GUS or nptII). Yet another consideration in expression of foreign genes in plants is the level of stability of the transgenic genome, i.e., the tendency of a foreign gene to segregate from the population. If a selective marker is linked to the gene of interest, then selection can be applied to maintain the transgenic plant.

SUMMARY OF THE INVENTION

It therefore is an object of the present invention to provide a genetic construct which will allow for the expression of a heterologous aprotinin gene in plants.

It is another object of the present invention to provide a transgenic plant comprising the above genetic construct that will allow commercial production of aprotinin and which yields protein in native conformation at a substantial savings over conventional methodology.

It also is an object of the present invention to allow for tracking of unauthorized propagation of a plant by reference to a genetic map of the region where a heterozygotic aprotinin gene has been introduced.

It is a further object of the present invention to provide an approach to cloning a gene for high-level, heterologous expression, based on integration of the gene at a position analogous to that of an aprotinin gene in a high-expressing, transgenic plant.

In accomplishing these and other objectives, there has been provided, in accordance with one aspect of the present invention, an isolated DNA molecule comprising a heterologous nucleotide sequence encoding aprotinin operably linked to a promoter sequence to allow its expression in plants. In a preferred embodiment, the DNA molecule further comprises a selection marker gene operably linked to a promoter sequence to allow its expression in plants. In another preferred embodiment the DNA molecule incorporates plant-preferred codons. In still another preferred embodiment the DNA molecule further comprises an intron sequence or a peptide export signal sequence which modifies expression of the aprotinin-encoding sequence. In yet another preferred embodiment, the export signal sequence is a barley alpha amylase peptide export signal sequence. In a further preferred embodiment, the intron sequence is a plant ubiquitin intron sequence.

In accordance with a second aspect of the present invention, a transgenic plant is provided that contains a DNA molecule as described above. In a preferred embodiment, the transgenic plant is a corn plant. In another preferred embodiment, from the transgenic plant, at least 0.1% of total extracted protein is aprotinin. In a further preferred embodiment, the transgenic plant provided is of strain 46969, germplasm of which strain has been deposited under ATCC Accession No. 97327.

In accordance with a third aspect of the present invention, a method of producing aprotinin in commercial quantities is provided, comprising the steps of (i) providing biomass from a plurality of plants, of which at least certain plants contain a DNA molecule comprised of a heterologous nucleotide sequence coding for aprotinin, wherein said nucleotide sequence is operably linked to a promoter to effect expression of aprotinin by said certain plants; and (ii) extracting aprotinin from said biomass. In a preferred embodiment the biomass from which aprotinin is extracted is comprised of seeds.

In accordance with a fourth aspect of the present invention, a method of determining whether a first transgenic plant of unknown parentage is derived from a second transgenic plant is provided, comprising the steps of:

(a) making a genetic map of the integration region of the nucleotide sequence coding for aprotinin in the second transgenic plant;

(b) making a genetic map of the integration region of the nucleotide sequence coding for aprotinin in the first transgenic plant; and then (c) comparing the maps of steps (a) and (b) to ascertain whether the insertion sites are the same.

In accordance with a fifth aspect of the present invention, a method of expressing genes at high levels in a plant is provided, comprising the steps of:

(a) cloning from a transgenic plant that expresses high levels of aprotinin a chromosomal fragment comprising a heterologous DNA sequence coding for aprotinin;

(b) cloning a chromosomal fragment corresponding to the chromosomal fragment of step (a) from a plant that does not express heterologous aprotinin;

(c) constructing an expression vector comprising the chromosomal fragment isolated in step (b);

(d) preparing a construct of a gene desired to be expressed at high levels within the vector, wherein said gene is located within plant chromosomal fragment of the vector of step (c) at a position corresponding to the heterologous aprotinin gene;

(e) transforming the constructs in plant cells or tissue;

(f) propagating plants from the transformed cells or tissue; and (g) based on an assessment of expression level for the gene desired to be expressed at high levels, selecting at least one plant for further propagation to produce the gene product.

DETAILED DESCRIPTION OF THE PREFERRED EMBODIMENTS

Figures 1A, 1B:
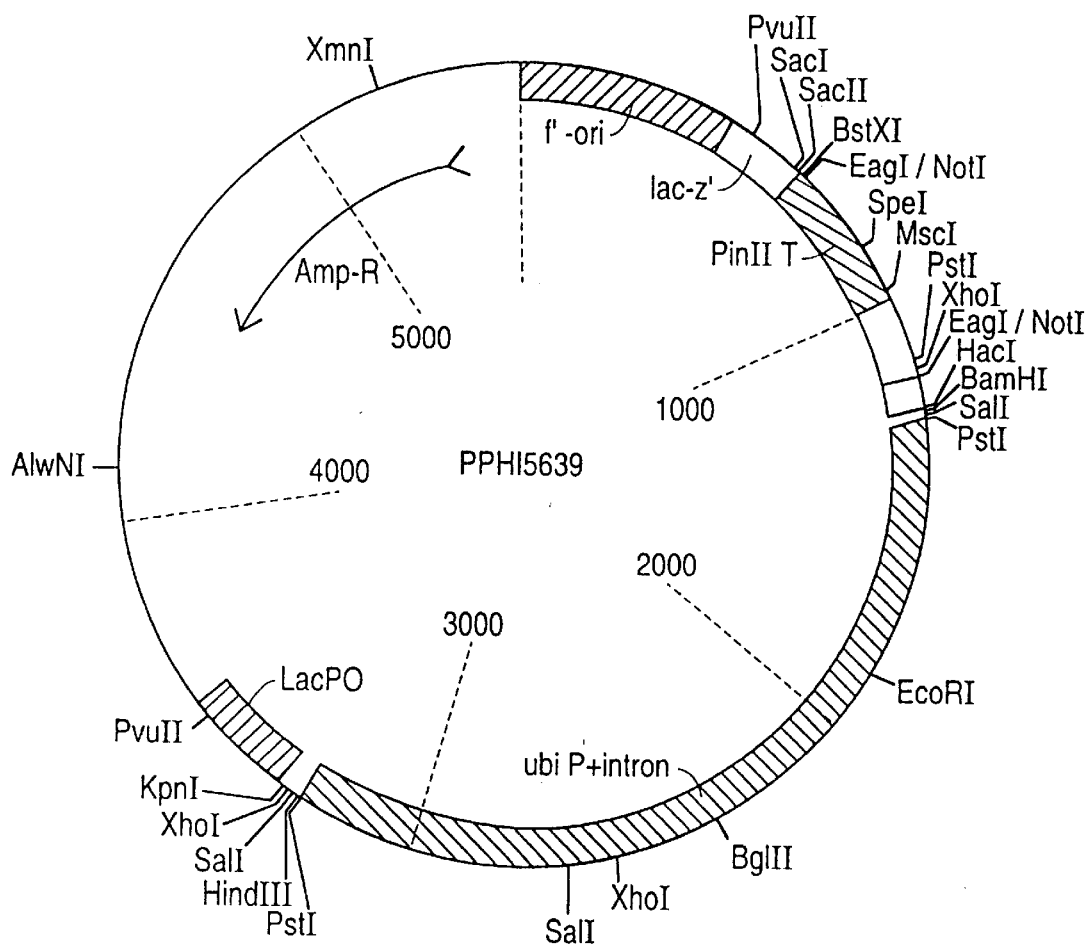
FIG. 1A shows the nucleotide sequence (SEQ ID NO: 1) of a BamHI/EcoRI fragment that contains the barley alpha amylase signal sequence fused to the aprotinin mature protein sequence, such that normal cellular processing will accurately cleave the molecule to yield mature active aprotinin. This sequence was synthesized and assembled as described in the specification. The BamHI and EcoRI restriction enzyme sites built in the sequence, at the 5' and 3' ends respectively, to facilitate further cloning are underlined.
FIG. 1B shows a restriction map of pPHI5639, the transformation vector in which the maize ubiquitin promoter (including its first exon plus first intron) was used to drive expression of the barley alpha amylase and of the aprotinin coding region, and which included the PinII transcription terminator sequence.
Figure 2:
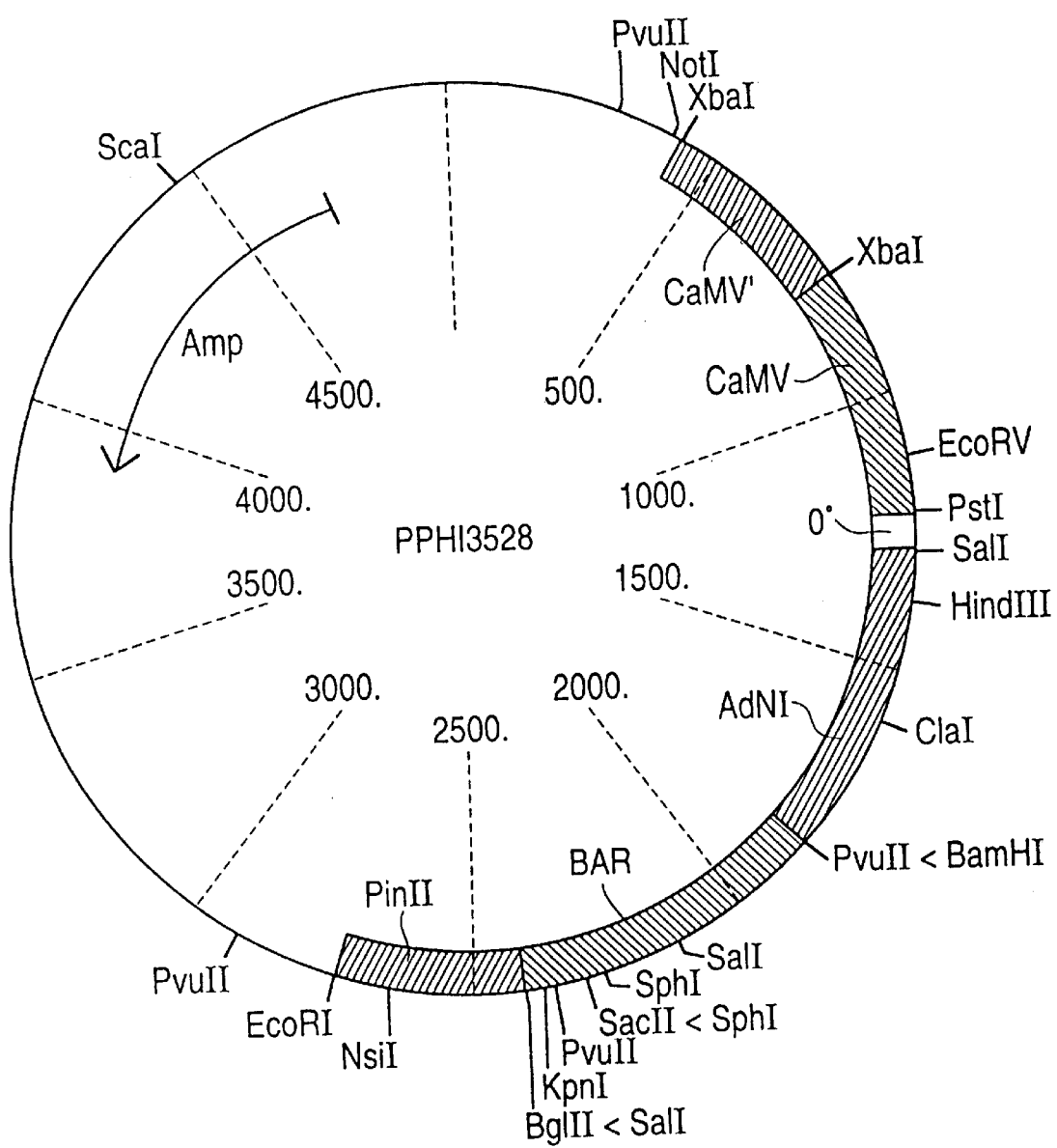
FIG. 2 shows plasmid pPHI3528 comprising the functional bar gene driven by a 35S promoter and further comprising a PinII transcription termination sequence.

The present inventors have determined that commercial production of aprotinin in plants is not only feasible but also offers substantial advantages over the conventional approach of obtaining the protein from bovine organs. Thus, current commercial sources of aprotinin have inherent disadvantages. Storage of raw materials is expensive. There is justified concern that aprotinin from animal sources would be contaminated by human pathogens if used as a therapeutic agent in humans. To address those issues, the current invention discloses a method of expressing aprotinin in plants. Plant tissue as raw material would be cheaper and more stable to store. Contamination by agents pathogenic to humans is unlikely from plant tissue. Aprotinin expressed in plants is active and is biochemically and functionally equivalent to aprotinin from bovine organs. Fortuitously, it has been determined that the serine-specific proteinase inhibitor aprotinin has potent insecticidal or larvicidal activity when administered enterically to insects such as European corn borer (ECB) and corn rootworm. Furthermore, aprotinin and highly similar serine proteinase inhibitors strongly potentiate the insecticidal activity of lectins such as wheat germ agglutinin. It appears that a transgenic plant expressing aprotinin would potentially be more resistant to plant pests such as ECB and corn rootworm.

In accordance with the present invention, therefore, a DNA molecule comprising a transformation/expression vector is engineered to incorporate aprotinin-encoding DNA. Extant knowledge concerning the respective sequences for aprotinin from bovine permits the isolation and cloning, by standard methodology, of the aprotinin gene. Another approach to the cloning of an aprotinin gene, especially from related species, might employ a functional assay based on the proteinase inhibitor activity of aprotinin. That would involve expression of a cDNA library and identification of a clone expressing a proteinase inhibitor. For either approach, the methodologies used would include identification of the gene by hybridization with probes, PCR, probe/primer/synthetic gene synthesis, sequencing, molecular cloning and other techniques which are well-known to those skilled in molecular biology.

In a preferred embodiment the aprotinin gene is put together by designing overlapping, complementary synthetic oligonucleotide sequences which could then be annealed and ligated together to yield the final gene. The nucleic acid sequence can be deduced by "reverse engineering" the known amino acid sequence of the bovine aprotinin gene and then generating a DNA sequence suitable for expression of this gene in maize. See Auerswald, *Bio. Chem. Hoppe-Seyler* 369 (suppl.): 27–35, (1988).

According to the present invention, the expression level of aprotinin can be increased by providing the genetic construct containing the aprotinin gene with a sequence encoding a peptide export signal sequence. The construct is made such that it results in a signal peptide fused to the N-terminal of the aprotinin mature protein sequence, allowing for normal cellular processing to cleave the protein molecule accurately to yield mature active aprotinin. Exemplary of suitable peptide export signal sequences is the barley alpha amylase signal sequence described by Rogers, *J. Biol. Chem.* 260: 3731–3738 (1985).

The expression levels of aprotinin also can be increased by providing the genetic construct containing the aprotinin gene with an intron sequence. In a preferred embodiment, the intron sequence added to the aprotinin gene in effect is the sequence of the first exon and first intron of plant ubiquitin gene. Cornejo et al., supra.

The methods available for putting together such a relatively short synthetic gene comprising the various modifications for enhancing the expression level described above—intron, peptide export signal sequence, codon usage—can differ in detail. But the methods generally include the designing and synthesis of overlapping, complementary synthetic oligonucleotides which are annealed and ligated together to yield a gene with convenient restriction sites for cloning. The methods involved are standard methods for a molecular biologist.

Once an aprotinin gene has been isolated and engineered to contain some or all features described above, it is placed into an expression vector by standard methods. The selection of an appropriate expression vector will depend upon the method of introducing the expression vector into host cells. A typical expression vector contains: prokaryotic DNA elements coding for a bacterial replication origin and an antibiotic resistance gene to provide for the growth and selection of the expression vector in the bacterial host; a cloning site for insertion of an exogenous DNA sequence, which in this context would code for aprotinin; eukaryotic DNA elements that control initiation of transcription of the exogenous gene, such as a promoter; and DNA elements that control the processing of transcripts, such as a transcription termination/polyadenylation sequence. It also can contain such sequences as are needed for the eventual integration of the vector into the chromosome.

In a preferred embodiment, the expression vector also contains a gene encoding a selection marker which is functionally linked to a promoter. For a general description of plant expression vectors and reporter genes, see Gruber et al., "Vectors for Plant Transformation," in METHODS IN PLANT MOLECULAR BIOLOGY AND BIOTECHNOLOGY 89–119 (CRC Press, 1993).

A promoter element employed to control expression of aprotinin and the reporter gene, respectively, can be any plant-compatible promoter. Those can be plant gene promoters, such as the promoter for the small subunit of ribulose-1,5-bis-phosphate carboxylase, or promoters from tumor-inducing plasmids of *Agrobacterium tumefaciens*, like that nopaline synthase and octopine synthase promoters, or viral promoters such as the cauliflower mosaic virus (CaMV) 19S and 35S promoters or the figwort mosaic virus 35S promoter. See international application WO 91/19806, for example, for a review of known plant promoters which are suitable for use in the present invention.

In a preferred embodiment, the promoter that controls expression of aprotinin is "tissue-preferred," in the sense that the aprotinin expression driven by the promoter is particularly high in the tissue from which extraction of the protein is desired; some expression may occur in other parts of the plant. Examples of known tissue-preferred promoters include the tuber-directed class I patatin promoter, Bevan et al., *Nucleic Acids Res.* 14: 4625–38 (1986); the promoters associated with potato tuber ADPGPP genes, Muller et al., *Mol. Gen. Genet.* 224: 136–46 (1990); the soybean promoter of β-conglycinin, also known as the 7S protein, which drives seed-directed transcription, Bray, *Planta* 172: 364–370 (1987); and seed-directed promoters from the zein genes of maize endosperm, Pedersen et al., *Cell* 29: 1015–26 (1982). In yet another preferred embodiment of the present invention, the exogenous, aprotinin-encoding DNA is under the transcriptional control of a plant ubiquitin promoter. Plant ubiquitin promoters are well known in the art, as evidenced by European patent application No. 0 342 926.

In another preferred embodiment, the selective gene is bar under the transcriptional control of the CaMV 35S promoter. See Kay et al. (1987), supra. The bar gene confers resistance to bialophos and to tabtoxin-β-lactam toxins. See Gordon-Kamm et al., *The Plant Cell* 2: 603 (1990); Uchimiya et al., *Biotechnology* 11: 835 (1993), and Anzai, et al., *Mol. Gen.* 219: 492 (1989).

In yet another preferred embodiment, separate expression vectors are constructed which contain a aprotinin gene under the control of ubiquitin promoter and the bar gene under the control of the CaMV 35S promoter, respectively. Those vectors then are cotransformed in a plant cell or tissue, as discussed in greater detail below. In another preferred embodiment, both the aprotinin and the bar gene, along with their transcriptional control elements, are located on one DNA molecule.

In accordance with the present invention, a transgenic plant is produced that contains a DNA molecule, comprised of elements as described above, which is integrated into its genome so that the plant expresses a heterologous, aprotinin-encoding DNA sequence. In order to create such a transgenic plant, the expression vectors containing a aprotinin gene can be introduced into protoplasts; into intact tissues, such as immature embryos and meristems; into callus cultures or into isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY 67–88 (CRC Press 1993), and by Phillips et al., "Cell/Tissue Culture and In Vitro Manipulation," in CORN AND CORN IMPROVEMENT 345–87 (American Society of Agronomy 1988). The reporter gene which is located on the DNA molecule allows for selection of transformants.

Methods for introducing expression vectors into plant tissue include the direct infection or co-cultivation of plant tissue with *Agrobacterium tumefaciens*. Horsch et al., *Science* 227: 1229 (1985). Preferably, a disarmed Ti-plasmid is used as a vector for foreign DNA sequences. Transformation can be performed using procedures described, for example, in European applications No. 116 718 and No. 270 822.

Other types of vectors can be used for transforming plant cells by procedures such as direct gene transfer, as described for example in PCT application WO 85/01856 and in European application No. 0 275 069; in vitro protoplast transformation, which is the subject of U.S. Pat. No. 4,684,611; plant virus-mediated transformation, illustrated in European application No. 0 67 553 and U.S. Pat. No. 4,407,956; and liposome-mediated transformation according to U.S. Pat. No. 4,536,475, among other disclosures. Standard methods for the transformation of rice are described by Christou et al., *Trends in Biotechnology* 10: 239 (1992), and by Lee et al., *Proc. Nat'l Acad. Sci. USA* 88: 6389 (1991). Wheat can be transformed by techniques similar to those employed for transforming corn or rice. Furthermore, Casas et al., *Proc. Nat'l Acad. Sci. USA* 90: 11212 (1993), describe a method for transforming sorghum, while Wan et al., *Plant Physiol.* 104: 37 (1994), describe a method for transforming barley. In a preferred embodiment, the transgenic plant of the present invention is maize. Suitable methods for corn transformation are provided by Fromm et al., *Bio/Technology* 8: 833 (1990), and by Gordon-Kamm et al., supra.

In general, direct transfer methods are preferred for the transformation of a monocotyledonous plant, particularly a cereal such as rice, corn, sorghum, barley or wheat. Suitable direct transfer methods include microprojectile-mediated delivery, DNA injection, electroporation, and the like. See, for example, Gruber et al., "Vectors for Plant Transformation," in METHODS IN PLANT MOLECULAR BIOLOGY AND BIOTECHNOLOGY; Miki et al., "Procedures for Introducing Foreign DNA into Plants," in METHODS IN PLANT MOLECULAR BIOLOGY AND BIOTECHNOLOGY; and Klein et al., *Bio/Technology* 10: 268 (1992).

Seed from strain 46969, a transgenic corn plant obtained by transformation with vectors comprising elements according to the present invention, has been deposited with the American Type Culture Collection (ATCC) in Rockville, Md., under Accession No. 97327. The vectors in question are designated pPHI5639 and pPHI3528. The former vector comprises the ubiquitin promoter, including the first exon and intron; the barley alpha amylase export signal sequence; an aprotinin-encoding sequence modified to reflect plant-preferred codon usage; and PinII as a transcription termination sequence. The other vector, pPHI3528, comprises a CaMV promoter operably linked to the bar gene.

Optimizing the level of aprotinin expression is a preferred course of action in implementing the present invention. To this end, it is useful to ascertain those constructs, transformed plant cells, and transgenic plants, respectively, that are associated with different levels of aprotinin expression. There are two assays that can be employed to determine expression levels in this regard. One is an enzymatic assay as described in Fritz et al., *Hoppe-Seylers Zeitschrift Fur Physiologishche Chemie* (Berlin) 345: 150–167 (1966) and Kassell, *Methods Enzy. XIX:* 844–852 (1970). This assay involves the measuring of aprotinin inhibition of the cleavage of Nx-Benzoyl-DL-Arginine-P-Nitroanilide to Nx-Benzoyl-DL-Arginine by trypsin.

Another assay for quantitation of aprotinin is an ELISA. A double antibody "sandwich" format is used. Both primary and secondary antibodies are rabbit polyclonal antibodies generated by contract for Pioneer Hybrid International by Bethyl Co., Montgomery, Tex. The secondary antibody is conjugated to biotin. Streptavidin-conjugated alkaline phosphatase is used to detect the antibody "sandwich." An aprotinin standard is used which is purchased from Sigma Chemical Co., St. Louis, Mo. The sandwich assay is a standard technique in the art.

The levels of expression of the gene of interest can be enhanced by the stable maintenance of the aprotinin gene on a chromosome of the transgenic plant. Use of a linked-genes construct, with herbicide resistance in physical proximity to the aprotinin gene, would allow for maintaining selective pressure on the transgenic plant population and for those plants where the genes of interest are not lost.

With transgenic plants according to the present invention, aprotinin can be produced in commercial quantities. Thus, the selection and propagation techniques described above yield a plurality of transgenic plants which are harvested in a conventional manner, and aprotinin then is extracted from a tissue of interest or from total biomass. Aprotinin extraction from biomass can be accomplished by known methods which are discussed, for example, by Heney and Orr, *Anal. Biochem.* 114: 92–6 (1981). It should be evident that, in any extraction methodology, there are inherent losses. In addition there are costs to be considered. Therefore a minimum level of expression of aprotinin is required for the process to be deemed economically worthwhile. The terms "commercial" and "commercial quantities" here denote a level of expression where at least 0.1% of the total extracted protein is aprotinin. Higher levels of aprotinin expression would make this undertaking yet more desirable.

According to a preferred embodiment, the transgenic plant provided for commercial production of aprotinin is maize. In another preferred embodiment, the biomass of interest is seed.

For the relatively small number of transgenic plants that show higher levels of expression, a genetic map can be generated, primarily via conventional RFLP and PCR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–84 (CRC Press, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR and sequencing, all of which are conventional techniques.

As discussed above, the location on the chromosome of an integrated, aprotinin-encoding DNA sequence can explain variation in the level of aprotinin expression obtainable with plants produced according to the present invention. Genetic mapping can be effected, first to identify DNA fragments which contain the integrated DNA and then to locate the integration site more precisely. This further analysis would consist primarily of DNA hybridizations, subcloning, and sequencing. The information thus obtained would allow for the cloning of a corresponding DNA fragment from a plant not engineered with a heterologous aprotinin gene. (In this context, "corresponding" denotes a DNA fragment that hybridizes under stringent conditions to the fragment containing the aprotinin gene.) The cloned fragment can be used for high level expression of another gene of interest. This is accomplished by introducing the other gene into the plant chromosome, at a position and in an orientation corresponding to that of the heterologous aprotinin gene. The insertion site for the gene of interest would not necessarily have to be precisely the same as that of the aprotinin gene, but simply in near proximity. Integration of an expression vector constructed as described above, into the plant chromosome then would be accomplished via recombination between the cloned plant DNA fragment and the chromosome. Recombinants where the gene of interest resides on the chromosome in a position corresponding to that of the highly expressed aprotinin gene likewise should express the gene at high levels.

As stated above, proteinase inhibitors, especially aprotinin, were found to be insecticidal to ECB and corn rootworm when delivered enterically. Furthermore, plant lectins, such as wheat germ agglutinin, have insecticidal activity which is potentiated by coingestion of aprotinin. This raises the possibility that transgenic plants comprising an aprotinin gene would be resistant to certain plant pests. A listing of the better documented ECB or corn rootworm interactions with plants includes such plants of current interest as corn, wheat and sorghum. Furthermore, complete listings as to what pests are susceptible to aprotinin and which plants may host those pests can be extended by experimentation. The following examples are illustrative but not limiting of the present invention.

EXAMPLE 1

Construction of Expression Vectors Containing the Aprotinin and Bar Genes

A gene optimized for expression of aprotinin protein in maize was generated and put together by designing overlapping, complementary synthetic oligonucleotide sequences containing compatible restriction site termini, which could then be annealed and ligated together to yield the final gene. The optimized DNA sequence was arrived at by "reverse engineering" from the known amino acid sequence of bovine aprotinin. See Auerswald, Bio. Chem. Hoppe-Seyler 369 (suppl.): 27–35 (1988). A DNA sequence was generated incorporating plant preferred codons. To determine the codon frequency, a codon bias table for maize was employed, wherein the amino acid codons occurring with a higher frequency in native maize genes were used, while infrequently used or unused codons were avoided. Additionally, a DNA sequence encoding the barley alpha amylase peptide signal sequence was generated using the same approach, and ligated to the 5' terminus of the aprotinin gene, in such a way that normal cellular processing of the translated pre-aprotinin protein would accurately cleave the signal sequence yielding mature aprotinin protein. This signal sequence was included based on the prediction that higher levels of aprotinin expression could be obtained if newly synthesized aprotinin protein was targeted to the extracellular compartment. The resultant signal sequence/aprotinin fragment (FIG. 1A) was cloned into the vector pGEM4Z (Promega Corporation, Madison, Wis.) as a BamHI/EcoRI fragment to generate pPHI5532. A BamHI/EcoRV fragment from pPHI5532 was then subcloned in another plasmid between the maize ubiquitin 5' region (including the promoter, the first exon and first intron) and the PinII transcription termination region, to generate pPHI5639 (FIG. 1B).

An additional plasmid, pPHI3528 was constructed and used to select for bialaphos resistance. This plasmid consisted of 35S promoter linked to the bar gene and further comprising of a PinII transcription termination sequence.

EXAMPLE 2

Generation of Aprotinin-expressing, Transgenic Plants

Immature embryos of Hi-II were used as source tissue for particle bombardment-mediated transformation using a helium powered particle acceleration device (P DS 1000, Bio-Rad). The method of transformation was that described by Gordan-Kamm, et al., using bialaphos during selection.

Plants initially regenerated from selected embryogenic tissue are termed $T_0$. Subsequent generations are termed T1, T2 etc. Transgenic plants were either selfed or used as females in crosses with untransformed maize plants. Plants which survived selection were/ assayed by ELISA for expression of aprotinin. Seed of subsequent generations were also tested by ELISA to select the highest expressions.

EXAMPLE 3

Aprotinin Extraction

Table 1 shows a compilation of the biochemical characteristics of the aprotinin derived from corn and compared with commercially available aprotinin from Sigma Chemical Company, St. Louis, Mo. Antibody was generated in rabbits. As seen in Table 1, the aprotinin from the two sources was biochemically similar. This conclusion was further supported by partial N-terminal sequencing of the two proteins which revealed aprotinin from the two sources to contain identical aa sequence. The molecular weight was determined by gel electrophoresis, on 4–20% SDS-polyacrylamide gels from Novex, San Diego, Calif. Aprotinin from the two sources was run in parallel with protein molecular weight standards from Novex. Determination of the isoelectric point for both proteins was performed on a Pharmacia PhastSystem, Pharmacia, Piscataway, N.J. General methods of determining the isoelectric point of proteins are provided by Walker, "Isoelectric Focusing of Proteins in Ultra-Thin Polyacrylamide Gels," in METHODS IN MOLECULAR BIOLOGY, Walker (ed), 32: 59–65 (Humana Press 1994). Affinity-purified polyclonal antibodies against aprotinin identified aprotinin from both sources by western blot analysis. Tobwin et al., Pro. Natl. Acad. Sci. U.S.A., 76: 4350–4354 (1979).

TABLE 1

Biochemical analysis of aprotinin extracted from corn

|  | PURIFIED FROM CORN SEED | BOVINE APROTININ PURCHASED FROM SIGMA CHEM. CO. |
|---|---|---|
| Mol. Wt. | 6500 | 6500 |
| PI | 10 | 10 |
| Binds to Antibody | Yes | Yes |

EXAMPLE 4

Aprotinin Insecticidal Activity

Aprotinin was the most effective protease inhibitor against European corn borer with high mortality occurring during a bioassay where larvae ingested the treatment as part of its diet and the larvae was analyzed after seven days of treatment. The assay was done in duplicate. The results are shown in Table 2. Aprotinin was also shown effective against corn rootworm neonate larvae (Diabrotica undecimpunctata howardii) in similar bioassays, as seen in Table 3.

TABLE 2

Effect of aprotinin and other protease inhibitors (PI) on European corn borer neonate larvae

| Treatment | Weight | Reduction (fold) | % Mortality |
|---|---|---|---|
| Control | 5.2 | — | 0* |
| Aprotinin | — | — | 100 |
| Soybean PI (Bowman-Birk) | 4.7 | — | 0 |
| Soybean PI (Kunitz) | 3.9 | 1.3 | 9 |
| Chicken PI (Type IV) | 2.9 | 1.8 | 0 |

*Corrected mortality

All materials were tested at 20 mg PI/ml of diet

TABLE 3

Effect of aprotinin and other protease inhibitors (PI) on Corn rootworm neonate larvae

| Treatment | Weight | Reduction (fold) | % Mortality |
|---|---|---|---|
| Control | 3.3 | — | 0* |
| Aprotinin | 0.4 | 8 | 60 |
| Soybean PI (Bowman-Birk) | 2.4 | 1.5 | 50 |
| Crystatin | 2.5 | 1.4 | 30 |

*Corrected mortality

All materials were tested at 20 mg PI/ml of diet

Example 5

Insecticidal Effect of a Combination of Aprotinin and Wheat Lectin

Tests were performed employing wheat germ agglutinin (WGA), aprotinin, and combinations of the two in 7-day bioassays performed as described in Example 4. The results are shown in Table 4. When the wheat lectin was replaced with Bauhinea purpurea lectin, similar results were also obtained. Replicated, 7-day bioassays were also performed to measure effects on growth. Results are shown in Table 5. The weight and weight reduction were significantly different from all other weights and reductions at $p<0.05$. The foregoing results indicate a synergy between aprotinin and insecticidal lectins in combination, both in terms of mortality and growth inhibition. Based on results with other combinations of insecticidal compounds, an additive or neutral effect would have been expected.

TABLE 4

Effect of WGA and aprotinin on European corn borer neonate larvae

| Treatment | Expected mortality from % Mortality | Aprotinin Addition |
|---|---|---|
| Control | — | 0 |
| 1. WGA 0.10 mg/ml | 10 | — |
| 2. WGA 0.15 mg/ml | 15 | — |
| 3. WGA 0.20 mg/ml | 20 | — |
| 4. WGA 0.25 mg/ml | 25 | — |
| 5. Aprotinin 0.25 mg/ml | 15 | — |
| 6. Aprotinin 0.5 mg/ml | 10 | — |
| 7. Aprotinin 1.0 mg/ml | 25 | — |
| 8. Aprotinin 2.0 mg/ml | 30 | — |
| Combinations | | |
| 4 + 8 | 55 | 90 |
| 3 + 7 | 45 | 80 |
| 2 + 7 | 40 | 75 |
| 3 + 5 | 35 | 70 |
| 3 + 6 | 30 | 70 |
| 2 + 6 | 25 | 55 |

TABLE 5

Effect of aprotinin and WGA combinations on ECB growth

| Treatment | Weight | (fold reduction) |
|---|---|---|
| Control | 10.5 | — |
| 1. Aprotinin 0.1 mg/ml | 7.8 | 1.3 |
| 2. WGA 0.1 mg/ml | 10.3 | — |
| 1 + 2 | 4.2 | 2.4 |

What is claimed is:

1. An isolated DNA molecule comprising a heterologous nucleotide sequence encoding aprotinin operably linked to a promoter sequence to allow its expression in plants.

2. The DNA molecule of claim 1, wherein said molecule further comprises a selection marker gene operably linked to a promoter sequence to allow its expression in plants.

3. A DNA molecule according to claim 1, wherein said aprotinin-encoding sequence incorporates plant-preferred codons.

4. A DNA molecule according to claim 1, wherein said molecule further comprises an intron sequence or a peptide export signal sequence which modifies expression of said aprotinin-encoding sequence.

5. An isolated DNA molecule according to claim 4, wherein said export signal sequence is a barley alpha amylase peptide export signal sequence.

6. An isolated DNA molecule according to claim 4, wherein said intron sequence is a plant ubiquitin intron sequence.

7. A transgenic plant stably transformed with a DNA molecule comprising a heterologous nucleotide sequence encoding aprotinin operably linked to a promoter sequence to allow its expression in plants such that the aprotinin expressed in the plant is capable of protease inhibition.

8. A transgenic plant according to claim 7, wherein said plant is a corn plant.

9. A transgenic plant according to claim 7, wherein at least 0.1% of total extracted protein is aprotinin.

10. A transgenic plant according to claim 7, wherein said plant is of strain 46969, germplasm of which strain has been deposited under ATCC Accession No. 97327.

11. A method of producing aprotinin in commercial quantities, comprising extracting aprotinin form a biomass of a plurality of plants, wherein at least some of the plants of the plurality express a DNA molecule comprised of a heterologous aprotinin-encoding nucleotide sequence and a promoter operably linked to said aprotinin-encoding sequence to effect expression of aprotinin.

12. The method according to claim 11 wherein said biomass is comprised of seed.

13. The method according to claim 11 wherein at least 0.1% of total extracted protein in said biomass is aprotinin.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGATCCCAAC  AATGGCCAAC  AAGCACCTGA  GCCTCTCCCT  CTTCCTCGTG  CTCCTCGGCC      60

TCTCCGCCTC  CCTCGCCAGC  GGCCGCCCGG  ACTTCTGCCT  CGAGCCGCCA  TACACCGGAC     120
```

| | | | | | | |
|---|---|---|---|---|---|---|
| CCTGCAGGGC | CAGGATCATC | CGCTACTTCT | ACAACGCCAA | GGCCGGCCTC | TGCCAGACCT | 180 |
| TCGTGTACGG | AGGCTGCCGC | GCCAAGCGCA | ACAACTTCAA | GAGCGCTGAG | GACTGCGAGC | 240 |
| GCACCTGCGG | AGGCGCCTGA | TATCGTCGAC | GAATTC | | | 276 |